United States Patent [19]
Duvick et al.

[11] Patent Number: 5,962,304
[45] Date of Patent: Oct. 5, 1999

[54] ZEARALENONE DETOXIFICATION COMPOSITIONS AND METHODS

[75] Inventors: Jon Duvick, Des Moines; Tracy A. Rood, Johnston, both of Iowa

[73] Assignee: Pioneer Hi-Bred International, Inc., Des Moines, Iowa

[21] Appl. No.: 09/088,325

[22] Filed: Jun. 1, 1998

Related U.S. Application Data

[63] Continuation of application No. 08/753,316, Nov. 22, 1996, Pat. No. 5,846,812.
[51] Int. Cl.⁶ .............................. C12N 1/12; C12N 1/20; C12N 1/00
[52] U.S. Cl. .................................. 435/252.1; 435/253.2; 435/872
[58] Field of Search ................................ 435/267, 252.1, 435/872, 253.2

[56] References Cited

PUBLICATIONS

Kiessling et al. (1984) Appl. Environ. Microbiol. 47, 1070–1073.

Bergey's Manual of systematic bacteriology (Sneath et al. Eds., 1986) vol. 2, pp. 1475, 1478, 1479.

Kollarczik et al. (1994) Natural toxins 2, 105–110.

Ono et al. (1993) Patent Abstracts of Japan, vol. 17, No.413.

*Primary Examiner*—Ponnathapura Achutamurthy
*Assistant Examiner*—Elizabeth Slobodyansky

[57] ABSTRACT

The present invention provides a bacterial microorganism of the Rhodococcus or Nocardia species having the ability to degrade zearalenone.

3 Claims, No Drawings

ZEARALENONE DETOXIFICATION COMPOSITIONS AND METHODS

CROSS REFERENCE TO RELATED APPLICATION

This application is a continuation of application Ser. No. 08/753,316, filed Nov. 22, 1996, now U.S. Pat. No. 5,846,812.

TECHNICAL FIELD

The present invention relates generally to the detection and isolation of zearalenone-degrading organisms and to compositions and methods for the detoxification or degradation of zearalenone. This method has broad application in agricultural biotechnology and crop agriculture and in the improvement of food grain quality.

BACKGROUND OF THE INVENTION

Fungal diseases are common problems in crop agriculture. Many strides have been made against plant diseases as exemplified by the use of hybrid plants, pesticides and unproved agricultural practices. However, as any grower or home gardener can attest, the problems of fungal plant disease continue to cause difficulties in plant cultivation. Thus, there is a continuing need for new methods and materials for solving the problems caused by fungal diseases of plants. These problems can be met through a variety of approaches. For example, the infectious organisms can be controlled through the use of agents that are selectively biocidal for the pathogens. Another method is interference with the mechanism by which the pathogen invades the host crop plant. Yet another method, in the case of pathogens that cause crop losses, is interference with the mechanism by which the pathogen causes injury to the host crop plant. Still another method, in the case of pathogens that produce toxins that are undesirable to mammals or other animals that feed on the crop plants, is interference with toxin production, storage, or activity.

Within the Fusarium sp are several important pathogens of corn and other cereals in various countries. In corn, Fusarium is known to cause root, stem and ear rot that results in severe crop reduction. The etiology of Fusarium ear mold is poorly understood, although physical damage to the ear and certain environmental conditions can contribute to its occurrence(Nelson PE (1992) "Taxonomy and Biology of Fusarium moniliforme." Mycopathologia 117: 29–36). Fusarium may be isolated from most field grown maize, when no visible mold is present. The relationship between seedling infection and the stalk and ear diseases caused by Fusarium is not clear. Genetic resistance to visible kernel mold has been identified.(Gendloff E, Rossman E, Casale W, Isleib T, Hart P, 1986, "Components of resistance to Fusarium ear rot in field corn." Phytopathology 76: 684–688; Holley RN, Hamilton PB, Goodman MM, 1989, "Evaluation of tropical maize germplasm for resistance to kernel colonization by *Fusarium moniliforme*." Plant Dis 73: 578–580). The mycotoxins produced by the Fusarium species that infect plants may accumulate in infected plants or in stored grains, presenting serious health consequences for livestock, humans, and other consumers of meat or other food products of such livestock. Fusarium infection has been associated with chronic or acute mycotoxicoses in both farm animals and man (Botallico, et al.). An important mycotoxin that has been found to be produced by certain Fusarium sp. and has been identified in Fusarium-infected crops is zearalenone.

Zearalenone, produced mainly by *Fusarium graminearum* (perfect form is *Gibberella zeae*), occurs in Fusarium-infected corn and to a lesser extent in other starchy cereal seeds. Zearalenone has been detected in hay, feed, corn, sorghum, dairy rations and barley that caused toxicosis in livestock in various countries (Ueno, et al. CRC Critical Rev. Toxicol. 14:99, 1985). When consumed by swine, it may incite an estrogenic response, including infertility, reduced litter size and weak piglets (Mirocha, 1971). Zearalenone has also been shown to cause abortion, vomiting and diarrhea in animals that consume the mycotoxin (Kollarczik, 1994, Nat. Toxins 2:105). It is also physiologically active in cattle, rats, mice, guinea pigs, poultry and plants (Mirocha, 1971; Stob, 1992). In rats, it has been shown to be teratogenic (Ueno et al., Cancer Res. 36:445, 1976; Ueno et al., Cancer Res. 38:536, 1978). Zearalenone has also been shown to induce modulation of uterine tissues in mice (Ueno, et al. Jap. J. Exp. Med. 45:199, 1970).

There is a need in the art for novel methods with which zearalenone may be eliminated from a plant or harvested grain. It is considered important by those skilled in the art to continue to develop inventions in order to protect the final consumer of a plant or harvested grain. The present invention provides the reagents and methodologies necessary to ameliorate plants and harvested grains from zearalenone.

SUMMARY OF THE INVENTION

In one embodiment, the present invention provides a wild-type organism having the ability to degrade or detoxify zearalenone or structurally related mycotoxins. The present invention may further include a mutant of the wild-type organism that has the ability to degrade or detoxify zearalenone or structurally related mycotoxins. The present invention also provides a method for the isolation and utilization of a zearalenone-degradation gene encoding a gene product having the ability to degrade or detoxify zearalenone or structurally related mycotoxins. In another embodiment, the present invention provides for the generation of transformants into which the zearalenone-degradation gene has been introduced, thereby providing the ability to degrade or detoxify zearalenone or a structurally related mycotoxin to said transformants. The present invention further provides a method for detoxification of a plant pre- or post-harvest using a microbe having the ability to degrade or detoxify zearalenone or structurally related mycotoxins. The invention also provides a method for detoxification of a plant pre- or post-harvest using a zearalenone-degradation gene.

DISCLOSURE OF THE INVENTION

The present invention is based on the discovery of organisms with the ability to degrade the mycotoxin zearalenone. The present invention has resulted from a search for a biological means of detoxifying zearalenones and comprises several bacterial species, isolated from field-grown maize kernels, and capable of growing on zearalenone as a sole carbon source, degrading it partially or completely in the process.

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g. J. H. Langenheim and K. V. Thimann, Botany: Plant Biology and Its Relation to Human Affairs (1982) John Wiley; Cell Culture and Somatic Cell Genetics of Plants, Vol. 1 (I. K. Vasil, ed. 1984); R. V. Stanier, J. L. Ingraham, M. L. Wheelis, and P. R. Painter, The Microbial World, (1986) 5th Ed., Prentice-Hall; O. D. Dhringra and J. B. Sinclair, Basic Plant Pathology Methods, (1985) CRC Press; Maniatis, Fritsch & Sambrook, Molecular Cloning: A Laboratory Manual (1982); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); the series in Methods in Enzymology (S. Colowick and N. Kaplan, eds., Academic Press, Inc.); and Current Protocols in Molecular Biology (John Wiley & Sons, Inc. 1996).

In describing the present invention, the following terms will be employed, and are intended to be defined as indicated below.

A microbe is defined as any microorganism (including both eukaryotic and prokaryotic organisms) such as fungi, yeasts, bacteria, actinomycetes, algae and protozoa, as well as other unicellular structures capable of growth in culture.

A zearalenone-producing microbe is any microbe capable of producing the mycotoxin zearalenone or analogs thereof. Such microbes are generally members of the fungal genus Fusarium, as well as recombinantly derived organisms which have been genetically altered to enable them to produce zearalenone or analogues thereof.

By zearalenone degradation, degrading zearalenone or having the ability to degrade zearalenone is meant any modification or ability to make any modification to the zearalenone molecule or a structurally related mycotoxin which causes a decrease in or loss of its toxic activity. Such a change can comprise cleavage of any of the various bonds, oxidation, reduction, the addition or deletion of a chemical moiety, or any other change that affects the activity of the molecule. Furthermore, chemically altered zearalenone may be isolated from cultures of microbes that produce an enzyme of this invention, such as by growing the organisms on media containing radioactively-labeled zearalenone, tracing the label, and isolating the degraded toxin for further study. The degraded zearalenone may be compared to the active compound for its phytotoxicity or mammalian toxicity in known sensitive species, such as porcines.

By structurally related mycotoxin is meant any mycotoxin having a chemical structure related to a zearalenone or analog of zearalenone, as well as other a mycotoxin having a similar chemical structure that would be expected to be detoxified by activity of the zearalenone-degradative enzymes.

Harvested grain is defined as any form of grain which has been somehow removed from the environment in which it was grown. For example, harvested grain may comprise ear corn, or corn kernels, for example. Harvested grain may further comprise that in storage or that being processed. Processed grain is grain that has been through some form of processing and will be used in the production of food for human consumption or will be used as animal feed ("feed grain").

Within this application, plant refers to a photosynthetic organism including but not limited to an algae, moss, fern, gymnosperm, or angiosperm. Preferably, said plant is one from which feed grain (preferably for human or animal consumption) may be harvested ("harvested grain"). Most preferably, said plant includes any variety of corn (maize), wheat, sorgum, rice and barley.

A mature plant is defined as a plant in which normal development of all vegetative and reproductive organs has occurred.

A plant cell includes any cell derived from a plant, including callus as well as protoplasts, and embryonic and gametic cells.

A regenerable culture is defined as a cell or tissue culture that can be manipulated so as to allow regeneration of a plant.

A plantlet is defined as a plant sufficiently developed to have a shoot and a root that is asexually reproduced by cell culture.

Explant refers to a section or piece of tissue from any part of a plant for culturing.

The term callus and its plural calli refer to an unorganized group of cells formed in response to cutting, severing or other injury inflicted on plant tissue. Excised pieces of plant tissue and isolated cells can be induced to form callus under the appropriate culture conditions. Callus can be maintained in culture for a considerable time by transferring of subculturing parts of the callus to fresh medium at regular intervals. The transfer of callus to liquid medium leads to dispersion of the tissue and the formation of a plant cell suspension culture. Callus can be induced to undergo organized development to form shoots roots.

Embryoid is defined as a structure similar in appearance to a plant zygotic embryo.

Somatic hybrid and somatic hybridization are generally defined as stable combination of cellular material, be it protoplast/protoplast or protoplast/cytoplast combinations, and includes cybrids and cybridization.

A transgenic plant is defined as any plant or plant cell that has become transformed by the introduction, stable and heritable incorporation, into the subject plant or plant cell, of foreign DNA, i.e. DNA encoding a protein not normally found within that plant species.

A hormone is defined as any plant growth regulator that affects the growth of differentiation of plant cells. Such hormones included cytokinins, auxins and gibberellins, as well as other substances capable of affecting plant cells.

A gene product that confers a selective advantage to a plant is defined as any gene product which, upon expression in said plant, confers increased growth rate, yield of product or resistance to threats to said plant's ability to thrive including but not limited to a pathogen, pest, adverse weather condition, and herbicide relative to a plant that does not express said gene product.

A replicon is any genetic element (e.g., plasmid, chromosome, virus) that functions as an autonomous unit of DNA replication in vivo; i.e., capable of replication under its own control.

A vector is a replicon, such as a plasmid, phage, or cosmid to which antoher DNA segment may be attached so as to bring about the replication of the attached segment.

The term nucleotide sequence is defined as a DNA or RNA molecule or sequence, and can include, for example, a cDNA, genomic DNA, or a synthetic DNA.

A DNA fragment is defined as segment of a single- or double-stranded DNA derived from any source.

A DNA construct is defined a plasmid, virus, autonomously replicating sequence, phage or linear segment of a single- or double-stranded DNA or RNA derived from any source.

A heterologous region of a DNA construct is defined herein as an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacterium. Another example of a heterologous coding sequence is a construct where the coding seuqence itself is not found in nature (e.g., synthetic sequences having codons different from the native gene). Heterologous DNA also refers to DNA not found within the host cell in nature. Allelic variation or naturally occurring mutational events do not give rise to a heterologous region of DNA, as these terms are used herein.

The term polypeptide as used herein is used in its broadest sense, i.e., any polymer of amino acids (dipeptide or greater) linked through peptide bonds. Thus, the term polypeptide includes proteins, oligopeptides, protein fragments, analogues, muteins, fusion proteins and the like. The term also encompasses amino acid polymers as described above that include additional non-amino acid moieties. Thus, the term polypeptide includes glycoproteins, lipoproteins, phosphoproteins, metalloproteins, nucleoproteins, as well as other conjugated proteins. The term polypeptide contemplates polypeptides as defined above that are recombinantly produced, isolated from an appropriate source or synthesized.

A transcriptional regulatory region is defined as any element involved in regulating transcription of a gene, including but not limited to promoters, enhancers and repressors.

A gene promoter is defined as any element involved in regulating transcription of a gene, including but not limited to promoters, enhancers and repressors.

A gene expressed in a tissue-preferred manner is that which demonstrates a greater amount of expression in one tissue as opposed to one or more second tissues in a plant specimen.

The term operably linked refers to the combination of a first nucleic acid fragment representing a transcriptional control region having activity in a cell joined to a second nucleic acid fragment encoding a reporter or effector gene such that expression of said reporter or effector gene is influenced by the presence of said transcriptional control region.

An assayable product includes any product encoded by a gene that is detectable using an assay. Furthermore, the detection and quantitation of said assayable product is anticipated to be directly proportional to the level of expression of said gene.

A reporter construct is defined as a subchromosomal and purified DNA molecule comprising a gene encoding an assayable product.

An expression vector is defined as a subchromosomal and purified DNA molecule comprising a transcriptional regulatory region driving expression of a gene.

An effector gene is defined as any gene that, upon expression of the polypeptide encoded by said gene, confers an effect on an organism, tissue or cell.

Transformation refers to a method of introduction of DNA into a cell. Said introduction may include but is not limited to particle bombardment, lipofection, electroporation, viral or bacterial vector-mediated, and calcium phosphate mediated techniques.

The present invention comprises a methodology for the isolation of a microorganism having the ability to degrade zearalenone or a structurally related mycotoxin, isolation of a gene encoding a gene product having the ability to degrade zearalenone, a methodology for degradation of zearalenone or a structurally related mycotoxin on a plant in the field or post-harvest, a transgenic plant having the ability to degrade zearalenone and a method for generating said transgenic plant. Said microorganism may include but is not limited to bacteria and fungi.

In order to isolate said microorganism having the ability to degrade zearalenone or a structurally related mycotoxin, an assay was developed in which a microorganism is initially isolated from a source material. Said source material may comprise any plant or plant-associated material including but not limited to any green tissue such as the stalk, leaf, ear, kernel, or soil in close approximation to the plant. To identify a microorganism having the ability to degrade zearalenone, said microorganism may be cultured in media containing zearalenone as the sole carbon source. Zearalenone, following addition to media, is generally found in a crystalline form. As zearalenone is degraded by said microorganism, the zearalenone crystals disappear from said media. The assay is termed a "crystal disappearance" assay. Degradation of zearalenone may be confirmed using techniques including but not limited to thin layer chromatography.

An important utility for the present invention is the detoxification of zearalenone present upon or within a plant or grain following harvest. A suitable feed material or "sample", that may include but is not limited to cracked corn, chicken feed or corn meal, is spiked with a known amount of mycotoxin delivered in a suitable solvent, preferably ethanol, at an appropriate rate, preferably one ml solvent per gram, followed by sufficient mixing to distribute said mycotoxin throughout said material. A control sample receives solvent only. The final concentration of said mycotoxin is preferably between 0.1 and 1.0 mg per gram of feed material. The sample may then be air-dried to remove excess solvent. The sample is next inoculated with $10^5$–$10^7$ colony forming untis (cfu)/g of log-phase cells of a microorganism having the ability to degrade said mycotoxin, at a sufficient rate, preferably one ml cells per gram, followed by sufficient mixing to distribute said cells throughout said sample. A control sample may comprise cells that have been killed by heating, preferably to approximately 80° C. A control sample may further comprise cells of a microorganism that is not able to degrade said mycotoxin. Said sample is then placed into a container, said container is closed and incubated for a sufficient period of time at an appropriate temperature. Said period of time is preferably within the range of one day to two weeks and said temperature is preferably room temperature or approximately 28° C. Following incubation, the contents of said container is extracted in a suitable organic solvent (or organic aqueous mixture) for recovering said mycotoxin. The resulting extract is then concentrated and subjected to qualitative and quantitative analysis for the presence of said mycotoxin. The amount of said mycotoxin detected in said extract is then compared to the amount of said mycotoxin detected in said control sample, and the efficacy of removal of said mycotoxin expressed as a percent reduction in the level of said mycotoxin in said experimental extract as compared to the level of said mycotoxin in said control sample. In the instant invention, said mycotoxin is preferably zearalenone. This methodology allows for the degradation of zearalenone upon or within said harvested plant or grain, thus providing improved food grain quality and feed safety.

Another important utility for the present invention is the detoxification of zearalenone within or upon a plant in the field. A plant may be inoculated with a zearalenone-producing organism and then treated with an appropriate amount of bacteria having the ability to degrade zearalenone. The treatment may comprise application of a composition comprising an efficacious amount of an organism having the ability to degrade zearalenone to said plant whereby the zearalenone present is degraded. Preferably, said application consists of topically applying said composition upon the tissues of said plant, such that zearalenone upon said tissues is degraded. To generate a plant having the de novo ability to degrade zearalenone, a gene (the "gene of interest") encoding a gene product having the ability to degrade zearalenone may isolated from said organism having the ability to degrade zearalenone and utilized to generate a transgenic plant.

It is possible to utilize any of several widely-available methodologies well known to one skilled in the art to isolate the gene of interest and the techniques described herein are not meant to limit the present invention to any certain methodology. One such method involves the isolation of a microorganism having the ability to degrade zearalenone (a "degrader"), isolation and limited cleavage of genomic DNA from said microorganism into DNA fragments using a restriction enzyme, and transformation of said DNA into a microorganism lacking the ability to degrade zearalenone (a "non-degrader"). Provided the gene of interest is included within a particular DNA fragment, transfer of said fragment into a non-degrader will confer upon said non-degrader a "degrader phenotype" (defined herein as the ability to degrade zearalenone). Thus, a fragment of DNA comprising a gene encoding a gene product having the ability to degrade zearalenone may be identified. Said fragment may then be further digested into subfragments which may then be transformed into a non-degrader organism. In this manner, the subfragment comprising said gene of interest may be isolated. This cycle may be repeated to further localize said gene of interest. DNA sequence analysis of said subfragment may then identify a potential candidate for a zearalenone-degradation gene. The potential candidate may then be transformed into a non-degrader and assayed for the ability to confer upon said non-degrader the degrader phenotype. In this manner, a gene encoding a gene product having the ability to degrade zearalenone may be isolated and identified.

Another method that may be utilized to isolate said gene of interest is polymerase chain reaction (PCR)-based differential display analysis (Liang, et al. Science 257:967). This methodology involves the use of random oligonucleotide primers, PCR-amplification of reverse transcriptase (RT)-cDNA and comparison of patterns of expression between a first sample (preferably a degrader) and a second sample (preferably a non-degrader). Non-identical DNA banding patterns of DNA amplified from said samples indicate a difference in gene expression between samples. A DNA fragment corresponding to a band that exhibits said non-identical DNA banding pattern may then be isolated and utilized to isolate and identify a gene to which said DNA band corresponds. The technique for isolation and identification of said gene is widely available to one skilled in the art.

Another method for isolating said gene of interest is cloning by subtractive hybridization (Lee, et al. Proc. Natl. Acad. Sci. 88:2825). Antisense cDNA of sample A (preferably a non-degrader) and biotinylated-RNA of sample B (preferably a degrader) are hybridized. Biotinylated-RNA molecules of the degrader organism representing genes expressed in both the non-degrader organism and the degrader organism will hybridize to the complementary cDNA molecules of the non-degrader to form hybrids. Said hybrids are then destroyed by enzymatic treatment. The remaining biotinylated RNA molecules of the degrader organism represent those genes expressed at a higher level in said degrader than in said non-degrader. Said biotinylated RNA molecules are then purified and a cDNA library representing said remaining biotinylated RNA of said degrader is constructed. The genetic material within said cDNA library may represent genes that are preferentially expressed in the degrader organism.

A further method comprises screening of a cDNA library of a first sample (preferably a degrader organism) using labeled RNA representing a second sample (preferably a non-degrader organism). Genetic material of said cDNA library of said first sample that does not hybridize to said labeled RNA of said second sample may represent RNA species that are not expressed in said second sample. Said genetic material may then be transformed into a non-degrader organism and said organism is assayed for the ability to degrade zearalenone using as assay such as the crystal disappearance assay. The ability of said genetic material to confer upon a non-degrader organism said degrader phenotype indicates that said genetic material comprises a gene encoding a gene product having the ability to degrade zearalenone (a gene of interest).

A further method that may be utilized to isolate a gene encoding a gene product capable of metabolizing zearalenone comprises purification of the gene product using conventional protein purification techniques. Many different techniques are available to one skilled in the art for purification of said gene product, and the techniques described herein are not meant to limit the present invention to a certain methodology. An extract is prepared from a bacterial isolate known to have the ability to degrade or detoxify zearalenone. The extract is prepared using conditions that maintain the ability of the protein of interest to degrade zearalenone. Fractions of the extract are then separated based on a certain biochemical property or combination of properties of the proteins comprising said fractions. Such properties allow separation of proteins based on characteristics including but not limited to molecular size, charge, and conformation using techniques including but not limited to size-exclusion chromatography, ion exchange chromatography, reverse phase chromatography, precipitation, centrifugation, and electrophoresis. Proteins of the extracts that share certain properties are collected into fractions. Each of said fractions is then assayed for the ability to degrade zearalenone, allowing for identification of fractions comprising a protein having the ability to degrade zearalenone. This fraction may then be further separated into subfractions using any of the above-described or any other available techniques. The proteins comprising said subfractions may then be assayed for the ability to degrade zearalenone. Said subfractions may be further fractionated (ultimately providing a partially or completely purified protein) in order to increase the purity of the protein having the ability to degrade zearalenone.

Following partial or complete purification of a protein having the ability to degrade zearalenone, a probe useful in identifying the gene encoding said protein is generated. Said probe may comprise an oligonucleotide or an antibody. In order to generate an oligonucleotide probe, the partially or completely purified protein having zearalenone-metabolizing activity is subjected to partial or complete amino acid sequence determination using techniques widely available to one skilled in the art, including but not limited to Edman degradation. The partial amino acid sequence is determined and an oligonucleotide is designed based on the amino acid sequence determination. The methodology for designing an oligonucleotide based on amino acid sequence is widely available and well known to those skilled in the art. The oligonucleotide comprises a region substantially identical to codons which encode the amino acid sequence of said protein having the ability to degrade zearalenone. Said oligonucleotide probe may be utilized to screen a nucleic acid library representing the genetic material of an organism having the ability to degrade zearalenone. Multiple distinct oligonucleotides may be designed and utilized for screening said nucleic acid library in order to perform multiple sequential hybridizations to limit isolation of "false positive" samples. The methodology for screening genomic DNA libraries is well known to those skilled in the art. Alternatively, several of said oligonucleotides may be designed for use in PCR-mediated cloning of a gene encoding a gene product having the ability to degrade zearalenone. PCR amplification of genetic material is a well-known method widely available to one skilled in the art. Said oligonucleotides may be utilized to amplify genetic material comprising a gene encoding a gene product having the ability to degrade zearalenone. Said genetic material may be isolated from a degrader organism and subjected to PCR amplification using said oligonucleotides as primers.

An antibody probe may be generated and utilized to isolate the gene the gene of interest. The above-described partially or completely purified protein product having the ability to degrade zearalenone may be utilized to immunize an animal host resulting in the generation of an antibody that binds to said protein. Methodologies involved in immunizing an animal with a partially or completely purified protein preparation and isolating the resulting antibody are widely available and well known in the art. The animal host may include but is not limited to a rabbit, mouse, rat, hamster, or guinea pig. Said antibody may comprise a whole antibody or a fragment thereof. An antibody or antibody fragment may also be generated using a phage display system. This method may comprise the use of an affinity column onto which is adsorbed the purified protein having zearalenone-metabolizing activity or a fragment thereof. A phage capsid comprising an antibody or antibody fragment capable of binding to said protein is applied to said column resulting in the interaction of a ligand (preferably said purified protein) and said antibody or antibody fragment on the surface of said phage. The gene encoding said antibody or antibody fragment may then be isolated from said phage and utilized to generate sufficient quantities of said antibody or antibody fragment to be utilized as an antibody probe. Said antibody probe may then be tested for binding to the proteins within the fraction containing the partially or completely purified protein having zearalenone-metabolizing activity.

A method that may be utilized to test the specificity of the antibody preparation includes but is not limited to western blot, a well known methodology well known to one skilled in the art. Proteins within said fraction separated electrophoretically using a technique such as gel electrophoresis which is well known and widely available to one skilled in the art. Following separation of said proteins of said fraction, said proteins are transferred to a solid support such as nitrocellulose or PVDF membrane which is then probed with said antibody preparation.

Provided said antibody binds to a protein bound to said solid support, said antibody may be detected using any of several antibody detection techniques that are well known and widely available to those skilled in the art. One such detection method includes the use of a labeled secondary antibody that demonstrates reactivity against said antibody. Said secondary antibody may be coupled to a detectable probe such as a radioactive nucleotide, an enzyme or biotin. Upon binding of the labeled secondary antibody to the primary antibody, the labeled secondary antibody may be detected using any of several widely available detection methodologies. One such detection method is the Enhanced Chemluminescent Detection System available from Amersham Corp.

A further method for testing said antibody for reactivity against said protein is the ELISA assay, the methodology of which is well known and widely available to those skilled in the art. A sufficient amount of said fraction is applied to a well of an assay plate, allowing the proteins within said fraction to bind to said well. A protein to which the antibody preparation react are then detected by application of said antibody followed by detection of said antibody using the ELISA detection methodology.

An antibody having reactivity to a protein within said fraction may then be utilized to screen an expression library comprising a gene found within the genetic material of a degrader organism. Methods for isolation of clones from such a library using an antibody are well known and widely available to those skilled in the art. Screening of said genomic library is accomplished by plating an organism transformed with a plasmid or infected with a bacteriophage comprising a portion of said genomic library. The genomic library is prepared such that the transformed organism will express a protein encoded by a gene within said genomic fragments. Said organisms or said genomic fragments of said organisms are then transferred to a solid support such as nitrocellulose, nylon or PVDF membrane and probed with said antibody having reactivity to a protein or proteins within said fraction. An organism that expresses the protein or proteins of interest is detected by reactivity with said antibody. Such an organism may then be isolated and further screening performed to isolate a pure population of said organism carrying said genomic fragment encoding said protein or proteins of interest. Purification may require several cycles of screening. In this manner, it is possible to isolate a genomic fragment comprising genetic material comprising a gene encoding a gene product having the ability to degrade zearalenone.

Confirmation that said genetic material isolated by any of the above-described techniques is expressed in a degrader organism may be achieved using any of several widely available techniques well known to one skilled in the art. A method that may be utilized to determine the level of gene expression is the RNase protection assay (Melton, et al. Nuc. Acids Res. 12:7035). RNA from the samples to be compared is isolated and hybridized to a labeled antisense RNA probe corresponding to the genetic material comprising a gene encoding a gene product having the ability to degrade zearalenone (Summers, 1970, Anal. Biochem. 33:459; Thomas, 1980, PNAS 77:5201). This is followed by the addition of RNase which will degrade non-hybridized transcripts. RNA that has hybridized to said RNA probe is protected from degradation (termed protected transcripts) by the RNase while mRNA that has not hybridized to said RNA probe is degraded. The products are then separated by gel electrophoresis and protected transcripts detected using detection methods including but not limited to autoradiography. The relative intensity of the band corresponding to said protected transcript is proportional to the level of expression of gene said transcript represents in the organism.

An additional method by which the level of gene expression may be determined is the northern blot analysis (Alwine, et al. Proc. Natl. Acad. Sci. 74:5350). RNA from a sample is isolated and separated by gel electrophoresis. The separated RNA species are then transferred to a membrane and probed with a labeled nucleic acid probe that is complementary to RNA representing a gene of interest. Hybridization is detected using a detection method including but not limited to autoradiography. The intensity of the band corresponding to RNA representing a gene of interest is determined and is proportional to the level of gene expression in the sample. Preferably, one sample is a degrader organism and another sample is a non-degrader organism. The level of gene expression of said gene of interest in the degrader organism is preferably increased in said degrader organism as compared to said non-degrader organism.

It may then be useful to construct an expression vector for testing the ability of said genetic material to confer the ability to metabolize zearalenone upon a non-degrader organism following transformation with said gene. A transcriptional control region able to drive gene expression in said organism may be linked in cis to said genetic material. Said expression vector may then be transformed into an organism that does not have the ability to degrade zearalenone. Following transformation, a transformed organism may be tested for the ability to degrade zearalenone using an assay such as the crystal disappearance assay. The ability of said non-degrader to degrade zearalenone following transformation with said expression vector indicates that a zearalenone gene has been isolated.

An expression vector comprising a transcriptional regulatory region that drives gene expression in plants operably linked to said genetic material comprising a gene encoding a gene product having the ability to degrade zearalenone may also be constructed. Said expression vector may be transformed into a plant cell or plant tissue. The method utilized for transformation of various types of plant cells or plant tissues may comprise particle bombardment, liposome-mediated transformation, calcium phosphate-mediated transformation, bacterial- or viral-mediated gene transfer, electroporation, or Agrobacterium-mediated transformation. A plant cell or plant tissue may be transformed in vitro after excision from said plant. Following a defined period of time after transformation of said expression vector into said plant cell or plant tissue, said plant cell or plant tissue may be harvested and an assay capable of detecting said gene product having the ability to degrade zearalenone performed. Said assay may comprise direct detection using an antibody or other probe or indirectly by measuring the ability of an extract derived from said plant cell or plant tissue to degrade zearalenone.

A transgenic plant having a copy of said gene of interest incorporated into the genome of the plant may be generated. A regenerable culture of a plant may be transformed with an expression vector comprising a gene encoding a gene product having the ability to degrade zearalenone. The method utilized for transformation of said regenerable culture may comprise particle bombardment, liposome-mediated transfection, calcium phosphate-mediated transfection, bacterial- or viral-mediated gene transfer, electroporation, or Agrobacterium-mediated transformation. Following transformation, said regenerable culture may be regenerated into a mature transgenic plant. Harvest of a tissue from said transgenic plant may then be performed followed by assay of said tissue for the presence of said gene product having the ability to degrade zearalenone. Said assay may comprise direct detection using an antibody or other probe or indirectly by measuring the ability of an extract derived from said plant cell or plant tissue to degrade zearalenone.

Tests may be performed on said transgenic plant to determine the ability of said transgenic plants to degrade zearalenone in the field. Said transgenic plant may inoculated at an early stage with a zearalenone-producing organism. Said transfected plant may then be harvested and an inoculated portion assayed for the presence of zearalenone.

A further test of the ability of said transgenic plant to degrade zearalenone may comprise feeding of said transgenic plant or grain harvested from said transgenic plant to a test animal such as a pig. Zearalenone has been shown to incite adverse effects in pigs including but not limited to an estrogenic response including infertility, reduced litter size and weak piglets. Zearalenone has also been shown to be physiologically active in cattle, rats, mice, guinea pigs, and poultry, any of which may also be utilized as a test animal. Said transgenic plant may be inoculated with a zearalenone-producing organism and, at the appropriate time, the inoculated transgenic plant or harvested grain from said transgenic plants may be fed to a test animal or animals. As an experimental control, another animal or animals are fed a non-transgenic plant or harvested grain from said non-transgenic plant that have been inoculated with a zearalenone-producing organism in an identical manner to that of said transgenic plant. The test animal or animals may then be observed for the presence of any adverse effects known to be associated with exposure to zearalenone. The presence of said adverse effects in an animal fed said non-transgenic, inoculated plant or harvested grains from said plant, and the lack of said adverse effect in an animal fed said transgenic, inoculated plant or harvested grain of said plant indicates that expression of said gene encoding a gene product having the ability to degrade zearalenone in said transgenic plant confers the ability to degrade zearalenone to said plant.

This invention can be better understood by reference to the following non-limiting examples. It will be appreciated by those skilled in the art that other embodiments of the invention may be practiced without departing from the spirit and the scope of the invention as herein disclosed and claimed.

EXAMPLE I. ISOLATION OF BACTERIA THAT DEGRADE ZEARALENONE

Various sources of plant material that were likely to naturally contain zearalenone were collected as source material for screening. Wheat kernels (140 independent samples) infested with *Fusarium graminearum*, the causal agent of wheat scab, were obtained from a Pioneer Hi-Bred International, Inc. ("Pioneer") wheat breeding station in Indiana. Silage samples were obtained from the Microbial Genetics division of Pioneer Hi-Bred and compost samples from local residences (139 independent samples total). *Fusarium graminearum*-infested maize kernels were obtained from a Pioneer Gibberella zeae (*Fusarium graminearum*) disease nursery (121 independent samples).

The metabolism of zearalenone was measured using the crystal disappearance assay. Microbes were washed from the source material by placing a small amount in a seven milliliter Falcon tube and adding one to two milliliters sterile distilled water (producing "wash fluid"). Maize kernels were split with a razor blade and one to two kernels were used. Tubes were capped and shaken for one to three hours at room temperature. Zearalenone (Sigma Cat. No. Z0167) was prepared as a suspension in mineral salts medium, and was utilized as the sole carbon source. The zearalenone concentration utilized includes but is not limited to 0.75–1.0 milligrams/milliliter in mineral salts medium. The mineral salts medium was prepared by combination of reagents including but not limited to 1.0 g/L ammonium sulfate, 1.0 g/L sodium chloride, 1.0 g/L potassium phosphate, dibasic, 0.2 g/L magnesium sulfate. Sterilization of the solution was accomplished by filtration through a 0.2 micron filter, although various methods for sterilization are available to those skilled in the art. 100 microliters of zearalenone/ mineral salts suspension medium was added to each well of a microliter plate (96 well plate). One microliter of wash fluid from said source material was added to each well. Control wells received one microliter of water. After two weeks, one microliter from each well was transferred to a new microliter plate containing 100 microliters of zearalenone/mineral salts medium. The transfer was then repeated four weeks later. After six weeks, wells were scored for partial disappearance of zearalenone crystals. Typically, the small crystals had been solubilized and metabolized, and only the very largest zearalenone crystals remained. This effect was visualized using an inverted microscope or by examining the plate visually from the underside.

Crystal disappearance was verified by thin layer chromatography (TLC). Silica gel plates containing fluorescent indicator (Whatman 4410 222) were spotted with typically one microgram zearalenone (typically one microliter from assay plates or one microliter of a one miligram/milliliter standard solution). Plates were run using a solvent system of chloroform-ethyl alcohol 97:3. Zearalenone could be seen as a bright blue spot under short-wave UV. Microbial metabolism of zearalenone caused a gradual disappearance of the spot; spots with altered mobility in the TLC system were not detected using this method.

The instant invention comprises a biologically pure culture of a microorganism having the ability to degrade zearalenone. Said microorganism was isolated using the following procedure. One microliter was removed from each well in which degradation of zearalenone was observed and added to one milliliter of sterile water. Several ten-fold dilutions were made in sterile water, and 100 microliters from each dilution were plated and spread on YDP agar plates. YDP agar plates were prepared by combination of 10 grams yeast extract (Difco), 20 g Bacto peptone, 0.5 g dextrose, 15 g Bacto agar in water followed by sterilization by autoclaving. From these mixture culture spread plates, individual colonies were streaked for isolation on new YDP plates. An effort was made to choose at least one of every type of bacteria represented on the spread plates. Each bacterium was used to make a dilute suspension in sterile water, and one microliter of this suspension was used to inoculate microliter wells containing zearalenone in mineral salts as described above.

Initial characterization of bacteria was performed by Gram staining samples. More definitive identification was performed using a combination of techniques. Streak plates of individual bacterial colonies were sent to Microbe Inotech Laboratories, Inc. (St. Louis, Mo.) for tentative identification. The analysis included comparison of bacterial fatty acid methyl esters with Aerobe and Clinical Aerobe databases, and Biolog™ substrate utilization comparison with a Gram positive database. Results of such tests indicate that the bacterial isolate is likely of the Rhodococcus or Nocardia species. From a total of 386 samples, zearalenone-degrading bacteria were isolated from four independent sources of *Fusarium graminearum*-infested maize. The data is summarized below in Table 1. Each of the four samples were deposited on Oct. 15, 1996 (ATCC 55853, ATCC 55852, ATCC 55851) and Oct. 22, 1996 (ATCC 55856) with the American Type Culture Collection (ATCC; 12301 Parklawn Drive, Rockville, Md. 20852 USA) in accordance with the Budapest Treaty on the International Recognition of the Deposit of Microorganisms for the Purposes of Patent Procedure.

TABLE 1

Microbial isolates having the ability to degrade zearalenone

| ATCC # | Name | Tentative Identification | Source |
|---|---|---|---|
| 55856 | 2855.1 | *Rhodococcus globulerus* or *Rhodococcus erythropolis* | Moldy corn, Michigan |
| 55853 | ZEA(1)2906.C1 | *Nocardia globulera* or *Rhodococcus erythropolis* | Moldy corn, Michigan |
| 55852 | ZEA(1)2906.C4 | *Nocardia globulera* or *Rhodococcus erythropolis* | Moldy corn, Michigan |
| 55851 | ZEA(1)2906.A8 | *Rhodococcus erythropolis* | Moldy corn, Michigan |

EXAMPLE II. TREATMENT OF ZEAROLENONE-CONTAMINATED CORN

A. Treatment of Contaminated Corn in the Field

To test the ability of the bacteria isolated by the above-described methodology to degrade or detoxify zearalenone or its derivatives or analogs on maize, mature plants are inoculated with a zearalenone-producing Fusarium sp. and then treated with an appropriate amount of bacteria having the ability to degrade or detoxify zearalenone or its derivatives or analogs. The treatment consists of topically applying a composition comprising an efficacious amount of bacteria onto the tissues of the maize plant such that zearalenone, potentially including any derivatives or analogs of zearalenone, is partially or completely degraded or detoxified.

B. Treatment of Contaminated Corn after Harvest.

A one to ten gram sample of cracked corn is combined or "spiked" with a known amount of zearalenone in ethanol at a concentration of one gram zearalenone per ml of ethanol, followed by mixing to distribute the zearalenone throughout the mixture. A control sample or samples are mixed with solvent alone. The samples are then air-dried to remove excess solvent. The samples are then inoculated with $10^6$ cfu/g of log-phase cells of a microorganism having the ability to degrade zearalenone, designated 2855.1 (deposited with the ATCC under accession number ATCC 55856) at a rate of one ml cells per gram, and mixed well to distribute said cells within said sample. Controls are mixed with either cells of said microorganism (designated 2855.1, deposited with the ATCC under ATCC accession number 55856) that have been heated to 80° C., such that said cells are non-viable or with cells of a microorganism that does not have the ability to degrade zearalenone. Said mixture is placed in a container, which is then closed and incubated for two weeks at room temperature. At the end of the incubation period, the container is opened, and the entire contents extracted in a suitable organic solvent to recover the zearalenone. The extract is concentrated and subjected to qualitative and quantitative analysis for detection of zearalenone. The amount of zearalenone is determined and compared to controls. The efficacy of removal of zearalenone is determined by comparison of the percent reduction of the amount of zearalenone in the sample comprising the micoorganism having the ability to degrade zearalenone to the reduction (if any) of the amount of zearalenone present in said control sample. Microorganisms designated ZEA(1)2906C.1 (ATCC accession number 55853), ZEA(1)2906.C4 (ATCC accession number 55852), or ZEA(1)2906.A8 (ATCC accession number 55851) are also able to degrade zearalenone, and may be utilized for the above-described purpose.

EXAMPLE III. CLONING OF A ZEARALENONE-DEGRADATION GENE

Following isolation of a microorganism having the ability to degrade zearalenone (a "degrader"), the genomic DNA of said microorganism is isolated and treated with a restriction enzyme into DNA fragments. Said DNA fragments are then cloned into an expression vector having a transcriptional control region able to drive gene expression in bacteria. Said expression vector comprising said transcriptional control region and a DNA fragment of said degrader organism is then transformed into a bacteria lacking the ability to degrade zearalenone (a "non-degrader"). Following transformation, the non-degrader bacteria are tested for the ability to degrade zearalenone (defined as the "degrader phenotype").

The metabolism of zearalenone is measured using a crystal disappearance assay. Zearalenone (Sigma Cat. No. Z0167) is prepared as a suspension in mineral salts medium, and utilized as the sole carbon source. The zearalenone concentration is 0.75–1.0 milligrams/milliliter in mineral salts medium. The mineral salts medium is prepared by combination of 1.0 g/L ammonium sulfate, 1.0 g/L sodium chloride, 1.0 g/L potassium phosphate, dibasic, 0.2 g/L magnesium sulfate. Sterilization of the solution is accomplished by filtration through a 0.2 micron filter. 100 microliters of zearalenone/mineral salts suspension medium is added to each well of a microliter plate (96 well plate) containing one microliter of a media containing said non-degrader bacteria. After two weeks, one microliter from each well is transferred to a new microliter plate containing 100 microliters of zearalenone/mineral salts medium. The transfer is then repeated four weeks later. After six weeks, wells are scored for partial disappearance of zearalenone crystals. This effect is visualized using an inverted microscope or by examining the plate visually from the underside. Crystal disappearance is verified by thin layer chromatography (TLC). Silica gel plates containing fluorescent indicator (Whatman 4410 222) are spotted with one microgram zearalenone. Plates are run using a solvent system of chloroform-ethyl alcohol 97:3. Microbial metabolism of zearalenone causes a gradual disappearance of the spot; spots with altered mobility in the TLC system are not detected using this method.

Provided the gene of interest is included within a particular DNA fragment, transfer of said fragment into a non-degrader confers upon said non-degrader said "degrader phenotype". Thus, a fragment of DNA comprising a gene encoding a gene product having the ability to degrade zearalenone is identified. Said fragment is then subjected to DNA sequencing in order to identify the genes included within said fragment. Following identification of a gene encoding a gene product having the ability to degrade zearalenone within said fragment, said gene is isolated and an expression vector comprising said gene is constructed. Said expression vector is then transformed into non-degrader bacteria, and said bacteria are isolated and tested for expression of the degrader phenotype. The presence of said degrader phenotype in a transformed non-degrader indicates that said gene encodes a gene product having the ability to degrade zearalenone.

EXAMPLE IV. TRANSGENIC CORN HAVING ZEAROLENONE-DEGRADING ACTIVITY

To provide a maize plant having the ability to degrade zearalenone, a transgenic maize plant is generated by transformation of a zearalenone-degradation gene into a maize regenerable culture (preferably derived from maize that do not have the ability to degrade zearalenone) followed by regeneration of said regenerable culture into a mature transgenic maize plant. Said maize regenerable culture is transformed by particle bombardment with an expression vector comprising a zearalenone-degradation gene. Following regeneration of said mature maize plant, certain tissues of said transgenic plant are harvested and an assay capable of detecting the zearalenone-degradation gene product is performed. Said gene product is detected by measuring the zearalenone-metabolizing activity of transfected cell extracts or tissue extracts from transfected tissue segments by TLC using radiolabeled zearalenone.

The ability of the zearalenone-degradation gene to confer the degrader phenotype upon said transgenic maize is tested. The developing ears of said transgenic maize are inoculated at the early silking stage using toothpicks impregnated with *Fusarium graminearum*. The infected corn cobs are then machine harvested and the infected portions of the cob and kernels assayed for the presence of zearalenone. The ability of said gene to confer the ability to degrade zearalenone upon said transgenic maize is indicated by the lack of zearalenone in tissues of said transgenic maize. Non-transgenic maize are inoculated in an identical manner as said transgenic maize and zearalenone is detected in said non-transgenic maize.

A further test of the ability of the transgene to provide zearalenone-degradation activity to transformed maize plants includes feeding the transgenic maize to animals such as pigs. Said transgenic maize is inoculated with *Fusarium graminearum* and, at the appropriate time, the inoculated transgenic corn is harvested and fed to the test animals. As an experimental control, certain other animals are fed non-transgenic corn that has been inoculated in an identical manner to that of said transgenic maize and, at the appropriate time, said maize is harvested and fed to the test animals. The animals are studied for the presence of any of the above-described estrogenic effects of zearalenone including infertility, reduced litter size and weak piglets after eating the Fusarium-inoculated transgenic maize or the Fusarium-inoculated non-transgenic maize. While the presence of an estrogenic response is observed in animals fed said Fusarium-inoculated, non-transgenic maize, an estrogenic response is not observed in animals fed said Fusarium-inoculated, transgenic maize. The absence of the estrogenic response in animals fed said Fusarium-inoculated, transgenic maize indicates that expression of said zearalenone-degradation gene in said transgenic maize provides said transgenic maize with the ability to degrade zearalenone to a non-toxic level in and on tissues of said transgenic maize.

While a preferred form of the invention has been shown in the drawings and described, since variations in the preferred form will be apparent to those skilled in the art, the invention should not be construed as limited to the specific form shown and described, but instead is as set forth in the claims.

What is claimed is:

1. An isolated and biologically pure bacterium having the ability to degrade zearalenone wherein said bacterium is of the Rhodococcus species or the Nocardia species.

2. The bacterium of claim 1 wherein said bacterium is selected from the group consisting of *Rhodococcus globerulus*, *Rhodococcus erythropolis*, and *Nocardia globerula*.

3. The bacterium of claim 2 wherein said bacterium is selected from the group consisting of the bacterium deposited under ATCC accession number 55856, the bacterium deposited under ATCC accession number 55853, the bacterium deposited under ATCC accession number 55852, and the bacterium deposited under ATCC accession number 55851.

\* \* \* \* \*